United States Patent
Mizrahy et al.

(10) Patent No.: US 12,076,575 B2
(45) Date of Patent: Sep. 3, 2024

(54) METHOD FOR TREATMENT OF ERECTILE DYSFUNCTION

(71) Applicant: Inmode Ltd., Yokneam (IL)

(72) Inventors: Moshe Mizrahy, Tel Aviv (IL); Michael Kreindel, Ontario (CA)

(73) Assignee: Inmode Ltd., Yokneam (IL)

( * ) Notice: Subject to any disclaimer, the term of this patent is extended or adjusted under 35 U.S.C. 154(b) by 638 days.

(21) Appl. No.: 17/208,252

(22) Filed: Mar. 22, 2021

(65) Prior Publication Data
US 2022/0296910 A1 Sep. 22, 2022

(51) Int. Cl.
*A61N 1/40* (2006.01)
*A61N 1/06* (2006.01)

(52) U.S. Cl.
CPC ............... *A61N 1/403* (2013.01); *A61N 1/06* (2013.01)

(58) Field of Classification Search
CPC ...... A61N 1/40; A61N 1/403; A61N 1/36007; A61N 1/06
See application file for complete search history.

(56) References Cited

U.S. PATENT DOCUMENTS

2018/0064937 A1* 3/2018 Lischinsky .............. A61N 1/36

FOREIGN PATENT DOCUMENTS

CN            212415752 U  *  1/2021

* cited by examiner

*Primary Examiner* — Linda C Dvorak
*Assistant Examiner* — Kyle M. Brown
(74) *Attorney, Agent, or Firm* — ALLEN DYER ET AL.

(57) ABSTRACT

A method for treatment of erectile dysfunction uses radiofrequency (RF) energy applied to the patient in proximity to the penile bulb.

11 Claims, 5 Drawing Sheets

METHOD FOR TREATMENT OF ERECTILE DYSFUNCTION

FIELD OF THE INVENTION

The invention relates to a device for treatment erectile dysfunction creating revascularization in a penis using deep heating.

BACKGROUND OF THE INVENTION

Erectile dysfunction is a common problem for aged male individuals. The most popular solution for these patients is PDE5 inhibitors. However, not everyone responds to the medication and not everyone is satisfied with the solution because of the lack of spontaneity.

An alternative solution is using radiofrequency (RF) energy for tissue heating and improving blood circulation. U.S. Pat. Nos. 9,913,981 and 10,729,904 describe methods for delivering energy, non-invasively, to penile tissue comprising at least one of tunica albuginea and penile septum using a plurality of RF electrode pairs externally arranged along a circumference of the penis, wherein RF electrodes in each RF electrode pair of the plurality of RF electrode pairs contact the outer skin surface of the penis at a substantially opposite sides of the penis with respect to each other.

SUMMARY OF THE INVENTION

The present invention describes a method for delivery RF energy to the penile using large area electrodes positioning along the penis placing one polarity electrode at the distal part of the penis and second electrode under another portion of the penis, such as the bulb of the penis. The RF current flows between the first electrode and second electrode along the axes of the penis heating the entire length of the penile tissue.

Each electrode may have capacitive contact with the tissue. The electrode may be covered by a dielectric material isolating the electrode from direct contact with tissue. RF energy may be delivered through the displacement current in the dielectric layer. This method allows avoiding direct galvanic contact between the electrode and tissue and isolates the patient from the electronic circuit. The method may include using a simple inexpensive cover applied between the electrode and patient to avoid cross-contamination.

The RF current can be applied between a large electrode applied to the external penile area and a second return electrode applied to the skin of the patient. The method allows electrical current to flow through the penile structure located inside the body and warm it, improving blood circulation. In a preferred embodiment, the second electrode is applied below the bulbospongiosus muscle in the area between the penis and anus. The electrode applied to this area may have a convex surface for better contact with the tissue.

The frequency of RF current is high enough to allow the current to be delivered through the dielectric film from the electrode to the tissue.

RF frequency of 1 MHz or higher may be used to deliver energy efficiently to the tissue. The impedance of the dielectric layer is in opposite proportion to the frequency of RF energy. A dielectric film with a thickness of 100 microns and an area of 10 $cm^2$ has an impedance of about 720 Ohm at 1 MHz and 360 Ohm at 2 MHz.

The RF electrode can be located on an applicator applied to the patient. A conductive gel can be used for better coupling between the penis and the applicator. The applicator may comprise one or more thermal sensors to monitor tissue surface temperature during the treatment. A thermistor, thermocouple or optical sensors can be used as the temperature sensor. The applicator may include a disposable part which contacts the patient and a reusable part.

The applicator may have a semi-cylindrical concave surface on the disposable part which is applied to the larger surface area of the penis.

In one embodiment, the first electrode can be attached to the distal area of the penis while the second electrode can be attached to the body area in proximity to the bulb of the penis. The RF current flows from the distal area of the penis along the entire length of the corpora cavernosa and corpus spongiosum towards the bulb of the penis. Such a placement of the electrodes heats the entire length of penile tissue.

RF energy may be delivered slow enough to allow heat conductivity to homogenize the thermal effect over the treated volume. Slow buildup of the temperature allows more reliable measurements of the tissue temperature.

The disposable part can be designed as a flexible PCB having a conductive layer on one side and a non-conductive layer that contacts the tissue.

Alternatively, the disposable part can be made from a metal sheet shaped for better contact with penile tissue and coated with a dielectric material. The dielectric material is biocompatible for contacting the patient.

In another embodiment, electrodes can be made from a conductive material, such as metal, composite materials or plastic coated with a metalized layer.

Each of the electrodes can be structured from a few elements for adjusting the contact surface. A spring loading mechanism can be used for better contact of the electrode with the patient.

The device may include an RF generator, an applicator, a user interface, a microprocessor and a circuit for monitoring RF parameters, such as RF current, RF voltage, RF power and tissue impedance.

The microprocessor may have software for controlling delivery of RF energy and adjusting RF output according to measured RF parameters and tissue temperature.

The applicator can be connected with a harness to the console to be attached to the patient. Alternatively, the applicator can be part of the console, and the patient sits on the device above the applicator coupled to the treated area.

The RF current heats the tissue to stimulate revascularization, collagen production and blood circulation without thermal coagulation of the tissue. The heating temperature may be below 50° C. for peak temperature and below 45° C. for the average temperature.

The treatment time and number of treatments can be different depending on the severity of the problem. The applicator may be coupled to the patient, and the treatment time and required tissue temperature may be set by the medical professional, and the medical professional does not have to be in the room with the patient during the treatment. The treatment time can be varied from 5 min up to 90 min. Patient may have access to a button that pauses the treatment in case of discomfort or emergency.

There is provided in accordance with a non-limiting embodiment of the invention a method for treating erectile dysfunction including applying RF energy in combination with other type of heating including optical energy, ultrasound energy, microwave energy.

There is provided in accordance with a non-limiting embodiment of the invention a method for treating erectile dysfunction including stretching penile tissue while heating the penile tissue with RF energy, wherein a combination of the stretching and the thermal energy improves blood flow in the penile tissue to treat erectile dysfunction of the penile tissue, wherein the stretching opens compressed blood vessels and the penile tissue is heated to a heated temperature above normal body temperature. The stretching may be created by applying negative pressure to the penile tissue.

Using negative pressure allows penile tissue to fill with blood and increase its conductivity for RF current.

DETAILED DESCRIPTION OF THE PREFERRED EMBODIMENTS

Figure 1:
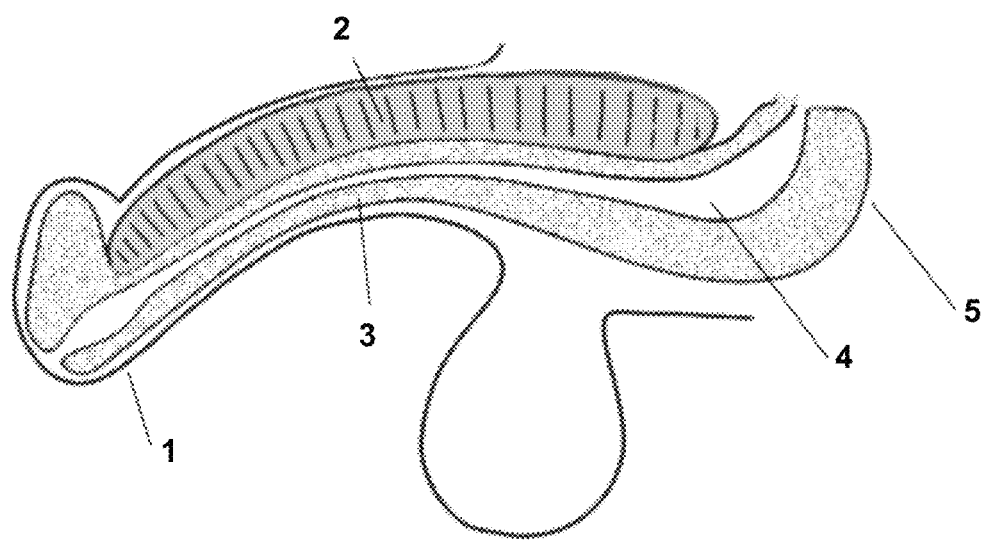
FIG. 1 is a schematic illustration of penis anatomy.

Referring to FIG. 1, a penile structure comprises outer part with distal end 1. The corpora cavernosa 2, corpus spongiosum 3 and urethra 4 extend along the length of the penis outside and inside the human body. The bulb 5 of the penis is located deep inside the body in proximity to the skin surface in the area between the testicles and anus.

Figure 2:
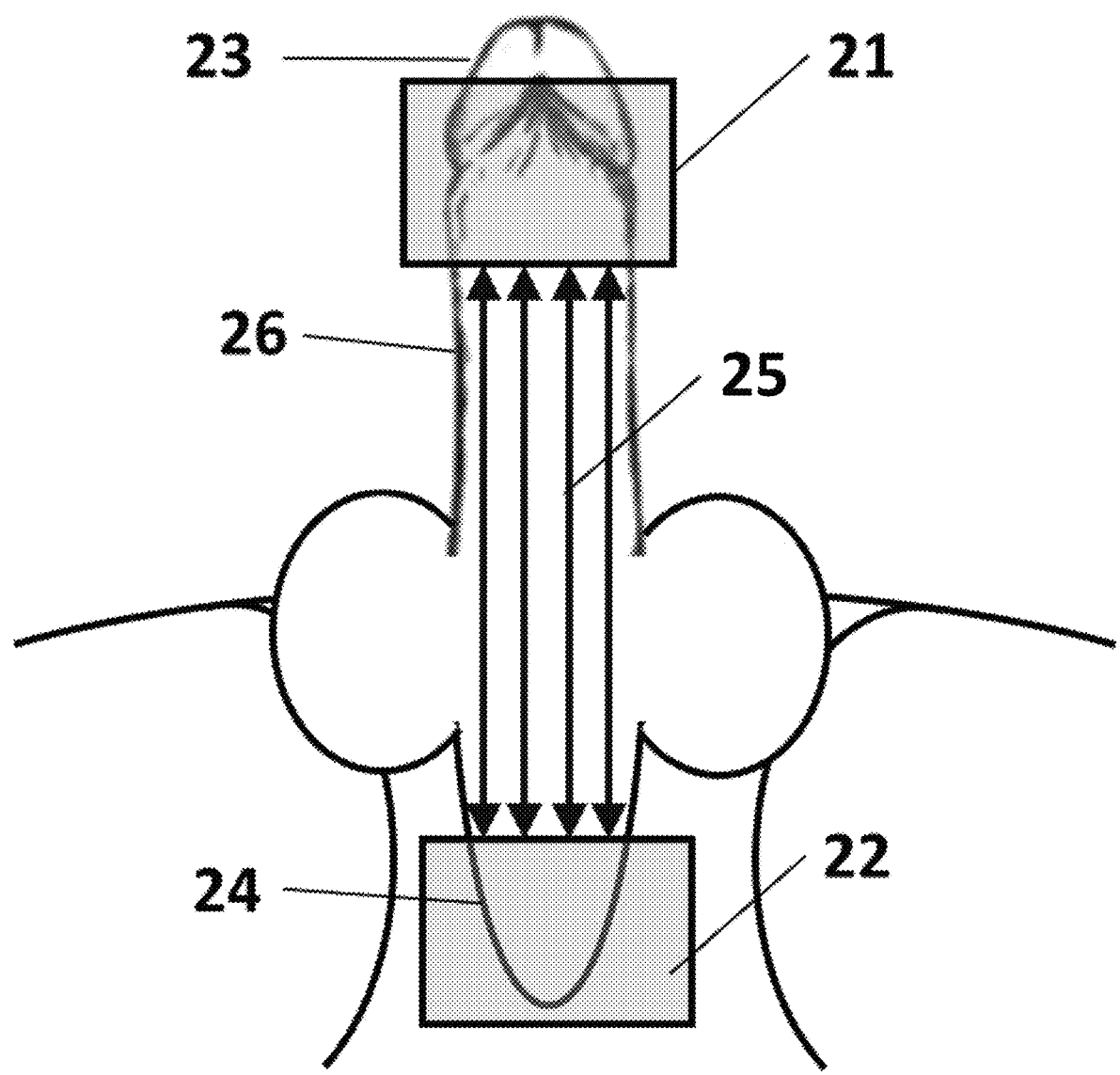
FIG. 2 is an illustration of treatment area with attached electrode.

FIG. 2 shows bottom view of a patient where first electrode 21 is attached to the tissue close to the distal end 23 of the penis while second electrode 22 is applied to the skin in vicinity of penis bulb 24. The RF current 25 flows between the first 21 and second 22 electrode along the penis 26 from distal end 23 toward the bulb 24 heating both external and internal part of the penis 26.

Figure 3:
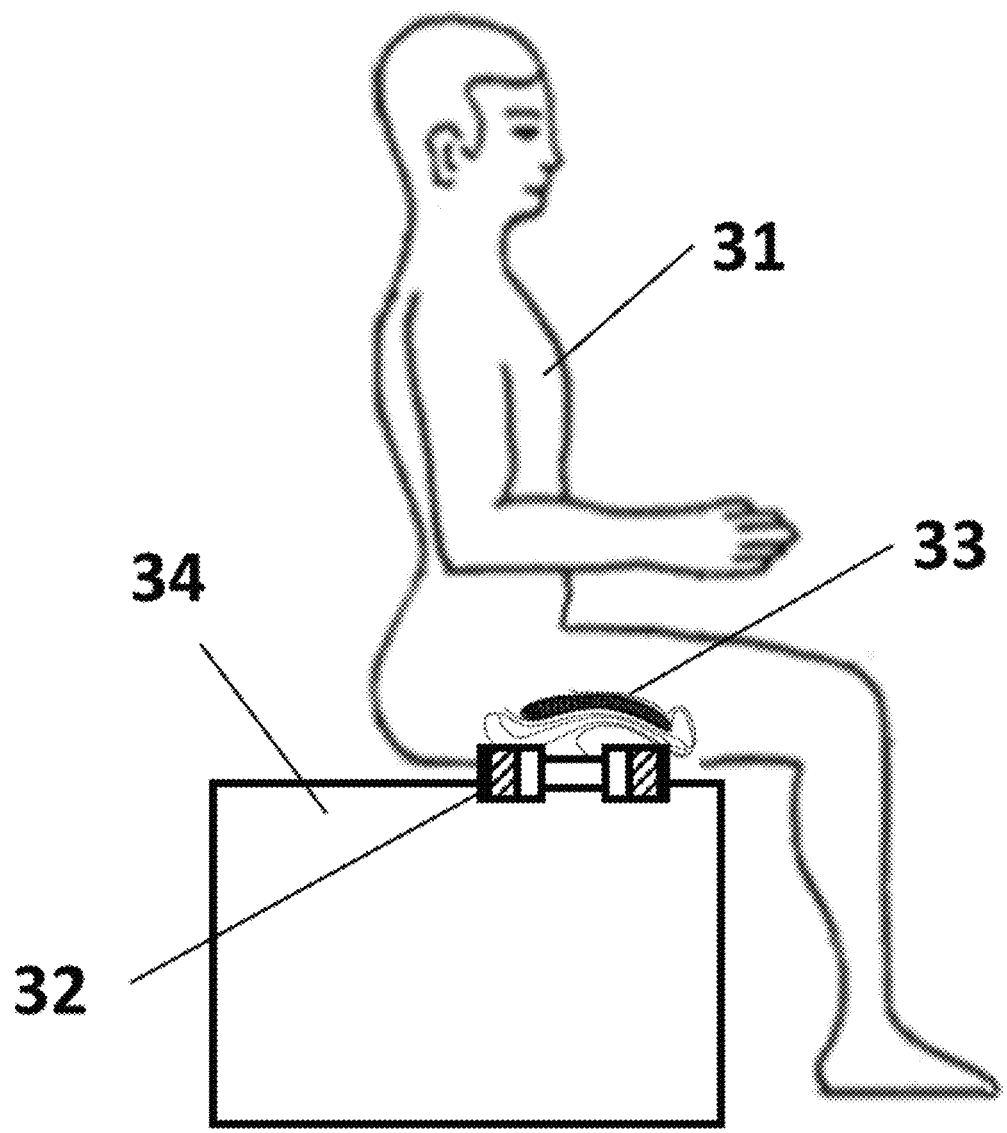
FIG. 3 is a schematic illustration of patient during the treatment.

FIG. 3 illustrates treatment of a patient 31 sitting on a device 34 with the penis 33 attached to the applicator 32. The device 34 comprises an RF generator and controlling system. The applicator 32 is connected mechanically and electrically to the device 34. The applicator can be moved in relation to the device to provide good contact with the penis distal end and the body area under the bulb of penis.

Figure 4:
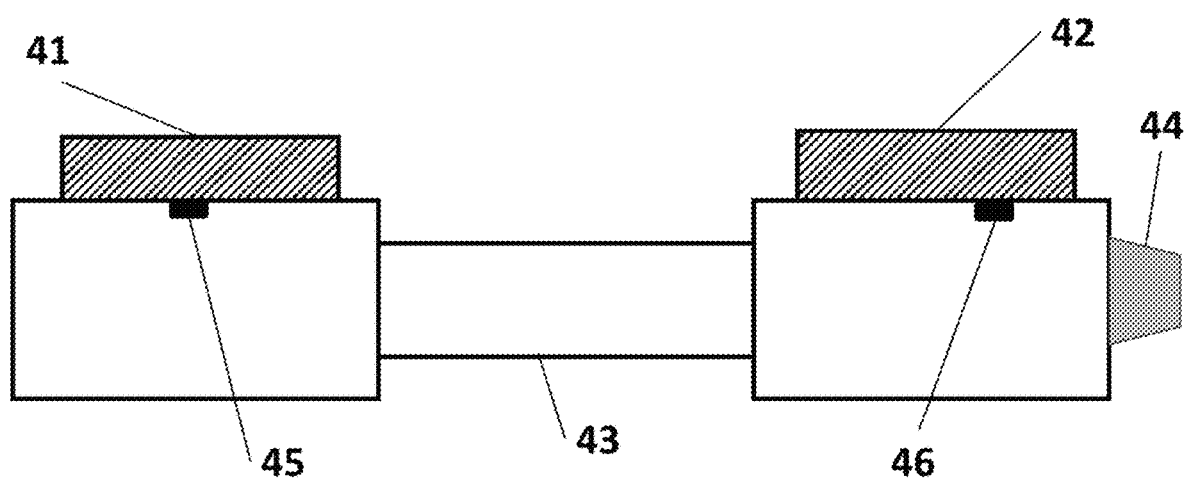
FIG. 4 is a schematic illustration of an applicator in accordance with a non-limiting embodiment of the invention.

FIG. 4 shows a schematic design of an applicator having a first electrode 41, which is applied to the distal end of the penis, and a second electrode 42 which is applied to the body in proximity to the penile bulb. The applicator has a telescopic mechanism 43, allowing the distance between electrodes to be changed so as to adjust the applicator for optimal RF energy delivery. The RF voltage from the device is delivered to the applicator. One RF polarity is connected to the first electrode 41 and a second RF polarity is connected to the second electrode 42. Temperature sensors 45, 46 are embedded into the applicator to measure tissue surface temperature at contact with each electrode. The first electrode 41 contacting the distal end of the penis has concave semi-cylindrical shape for better contact with the penis. The electrode 41 may be split into multiple elements for the better contacting the penile surface. The second electrode 42 has convex semi-cylindrical surface for contacting the body in proximity of the bulb. The electrode 42 can also be split to multiple elements for better contacting the body area.

Figure 5:
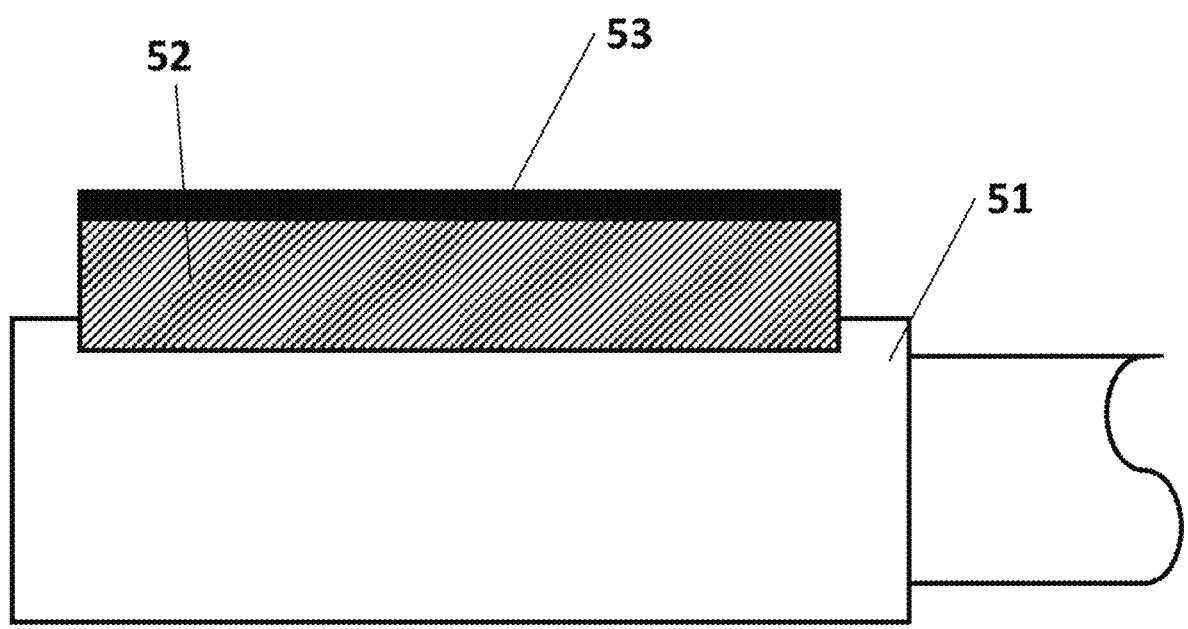
FIG. 5 is a schematic illustration of electrode coated with dielectric material in accordance with a non-limiting embodiment of the invention.

FIG. 5 shows a design of an applicator 51 with an RF electrode 52 for capacitive coupling with patient. The conductive electrode 52 is coated with thin dielectric film 53 allowing high frequency electrical current to be delivered to the patient and isolating the patient from low frequency current, minimizing the risk of electrical shock. The thickness of dielectric film is not more than 0.3 mm and ideally, it should be in the range of 50 microns to 200 microns.

Non-limiting parameters for the device of the invention are as follows:

1. RF average power is in the range of 2 W up to 70 W.
2. The RF frequency should be above 0.4 MHz and 2 MHz or higher for electrodes with capacitive coupling.
3. The treatment time is in the range of 5 minutes to 90 minutes.
4. The distance between electrodes is adjusted according to the individual anatomy of the patient.
5. The electrode applied the distal end of the penis has a concave shape.
6. The electrode contacting the body of the patient in proximity of penile bulb has a convex shape.

In contrast to the above-described invention, different shapes and structure of electrodes can be used.

What is claimed is:

1. A method for treating erectile dysfunction comprising: applying at least one first electrode to a body surface in proximity to a penile bulb; applying at least one second electrode at a distal end of a penis; applying radiofrequency (RF) current along a length the penis between the at least one first and second electrodes to increase a temperature of penile tissue above a body temperature; limiting RF energy to avoid thermal necrosis of the tissue; and maintaining penile tissue heating for predetermined period of time; wherein there are only first and second electrodes exclusively applied to a same side of the penis.

2. The method according to claim 1, wherein the increased temperature does not exceed 50° Celsius (C).

3. The method according to claim 1, wherein the RF current is applied through capacitive coupling.

4. The method according to claim 1, wherein either of the at least one first electrode or at least one second electrode includes a plurality of split electrodes.

5. A method for treating erectile dysfunction comprising: setting treatment parameters; applying an applicator having at least one first radiofrequency (RF) electrode to a body area in proximity to a penile bulb; adjusting a distance between the at least one first RF electrode applied in proximity to the penile bulb and at least one second electrode applied to a distal end of the penis; activating a device including an RF generator and connected to the first and second RF electrodes; and automatically adjusting delivered RF energy to fulfil a treatment protocol for a predetermined period of time; wherein there are only first and second RF electrodes exclusively applied to a same side of the penis.

6. The method according to claim 5, wherein the treatment parameters include at least one of the following: RF power, treatment time, and tissue temperature.

7. The method according to claim 5, wherein the treatment protocol includes a required tissue temperature and treatment time.

8. A method for improving blood supply in penile tissue comprising:

applying radiofrequency (RF) energy along a length of a penis between a penile bulb and a distal end of the penis; and adjusting treatment parameters automatically during the application of RF energy to maintain required tissue temperature; and wherein the RF energy is exclusively applied between electrodes applied to a same side of the penis.

9. The method according to claim 8, wherein the treatment parameters include RF power.

10. A method for treating erectile dysfunction comprising: setting radiofrequency (RF) treatment parameters; setting at least one RF electrode on a skin surface in proximity to a penile bulb; setting at least one another RF electrode at a distal end of a penis; activating a device for treatment of a patient while automatically maintaining a predetermined thermal protocol; maintaining a static position of the RF electrodes during the treatment; and disconnecting the electrodes from the patient at the end of the treatment; wherein there are only RF electrodes exclusively applied to a same side of the penis.

11. The method according to claim 10, wherein the thermal protocol includes a tissue temperature and a treatment time.

\* \* \* \* \*